US00PP34827P2

(12) United States Plant Patent
Berry

(10) Patent No.: US PP34,827 P2
(45) Date of Patent: Dec. 13, 2022

(54) ***HIBISCUS* PLANT NAMED 'JBG AH-51'**

(50) Latin Name: *Hibiscus rosa-sinensis*
Varietal Denomination: JBG AH-51

(71) Applicant: Capstone Plants, Inc., Grand Saline, TX (US)

(72) Inventor: James Berry, Emory, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 8 days.

(21) Appl. No.: 17/803,117

(22) Filed: Feb. 17, 2022

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257

CPC ... A01H 5/02; A01H 5/00; A01H 6/60; A01H 6/608
See application file for complete search history.

(56) References Cited

PUBLICATIONS

Monrovia 2022 Distinctive Selections, retrieved on Mar. 21, 2022, retrieved from the Internet at https://f.hubspotusercontent20.net/hubfs/1925176/2022%20DistinctiveSelectionsGuide_FINAL.pdf, 2 introductory pages and p. 15. (Year: 2022).*
Sparks Highlights from Cultivate'20 Virtual: New Products and New Educational Opportunities, Greenhouse Grower, retrieved on Mar. 21, 2022, retrieved from the Internet at https://www.greenhousegrower.com/management/highlights-from-cultivate20-virtual-new-products-and-new-educational-opportunities/, 7 pp. (Year: 2020).*

* cited by examiner

*Primary Examiner* — June Hwu
(74) *Attorney, Agent, or Firm* — The Webb Law Firm

(57) ABSTRACT

A new and distinct *Hibiscus* plant having white with pale yellow colored flowers and a burgundy colored throat.

2 Drawing Sheets

Botanical classification: *Hibiscus rosa-sinensis.*
Varietal denomination: 'JBG AH-51'.

BACKGROUND OF THE INVENTION

The present invention comprises a new and distinct *Hibiscus* plant having the varietal name 'JBG AH-51'. The new variety is the result of a planned breeding program with the purposes of developing *Hibiscus rosa-sinensis* plants that exhibit whitefly and leaf spot resistance, propagation and production efficiencies, durable and exotic flowers, and abundant flowering. 'JBG AH-51' is the result of a cross conducted in Grand Saline, Tex. between *Hibiscus rosa-sinensis* varieties 'JBG 14023' (female parent, U.S. Plant Pat. No. 31,303) and 'JBG 14003' (male parent, U.S. Plant Pat. No. 31,854). The new variety was selected in February of 2016 in Grand Saline, Tex. and the first asexual reproduction of the new variety was conducted by semi-hardwood cuttings in June of 2016 in Grand Saline, Tex. 'JBG AH-51' has been trial and field tested and has been found to retain its distinctive characteristics and remain true to type through successive propagations. The present invention has not been evaluated under all possible environmental conditions. However, it has been found to thrive in production and adapt well to the environment in Homestead, Fla. The phenotype may vary with variations in environment without a change in the genotype of the plant.

'JBG AH-51' is similar to its female parent in petal and eye flower color, as well as its upright growth habit. 'JBG AH-51' differs from its female parent in that the new variety exhibits darker green colored leaves with more serration, fringed flower petals, and flowers that point outwards instead of down. 'JBG AH-51' is similar to its male parent in dark green leaf color with abundant chlorophyll present and upright growth habit. 'JBG AH-51' differs from its male parent in flower coloration and having a lower bud count.

When 'JBG AH-51' is compared to *Hibiscus rosa-sinensis* variety having a commercial name of "Starstruck". (unpatented), both varieties have a main flower color of white and similar whitefly resistance. However, 'JBG AH-51' grows more upright, has darker leaves, and fewer and more exotic flowers than "Starstruck".

The following traits distinguish 'JBG AH-51' as a new and distinct cultivar from other *Hibiscus* varieties known to the breeder:

1. Moderate leaf serration;
2. Exotic flower coloration;
3. High growth rate; and
4. Moderate petal ruffling.

DESCRIPTION OF THE DRAWINGS

The accompanying photographic images illustrate the new variety at approximately three years of age, with the colors being as nearly true as is possible with color illustrations of this type.

DESCRIPTION OF THE PLANT

Figure 1:
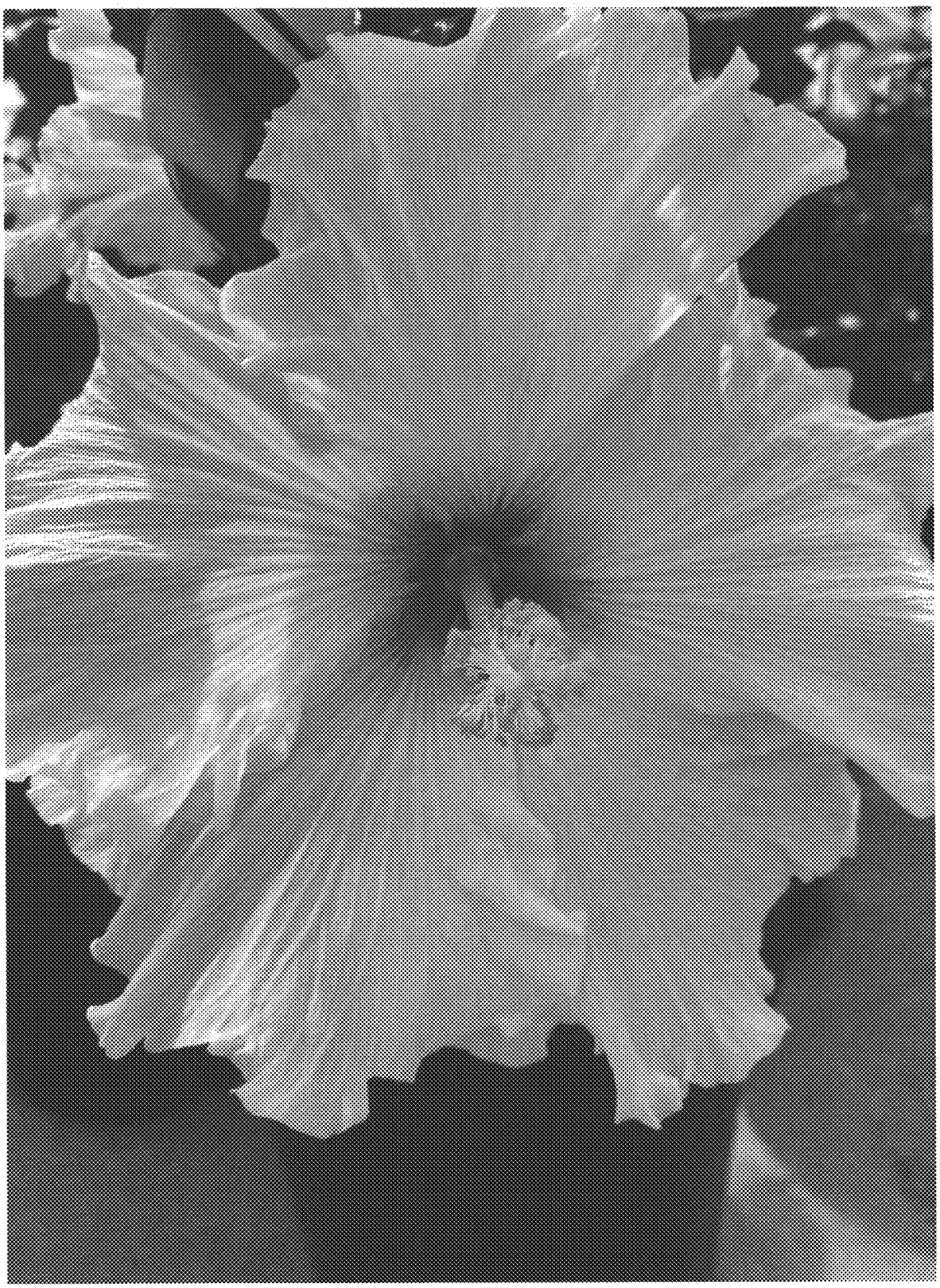
FIG. 1 illustrates a close-up view of a flower of the new variety.
Figure 2:
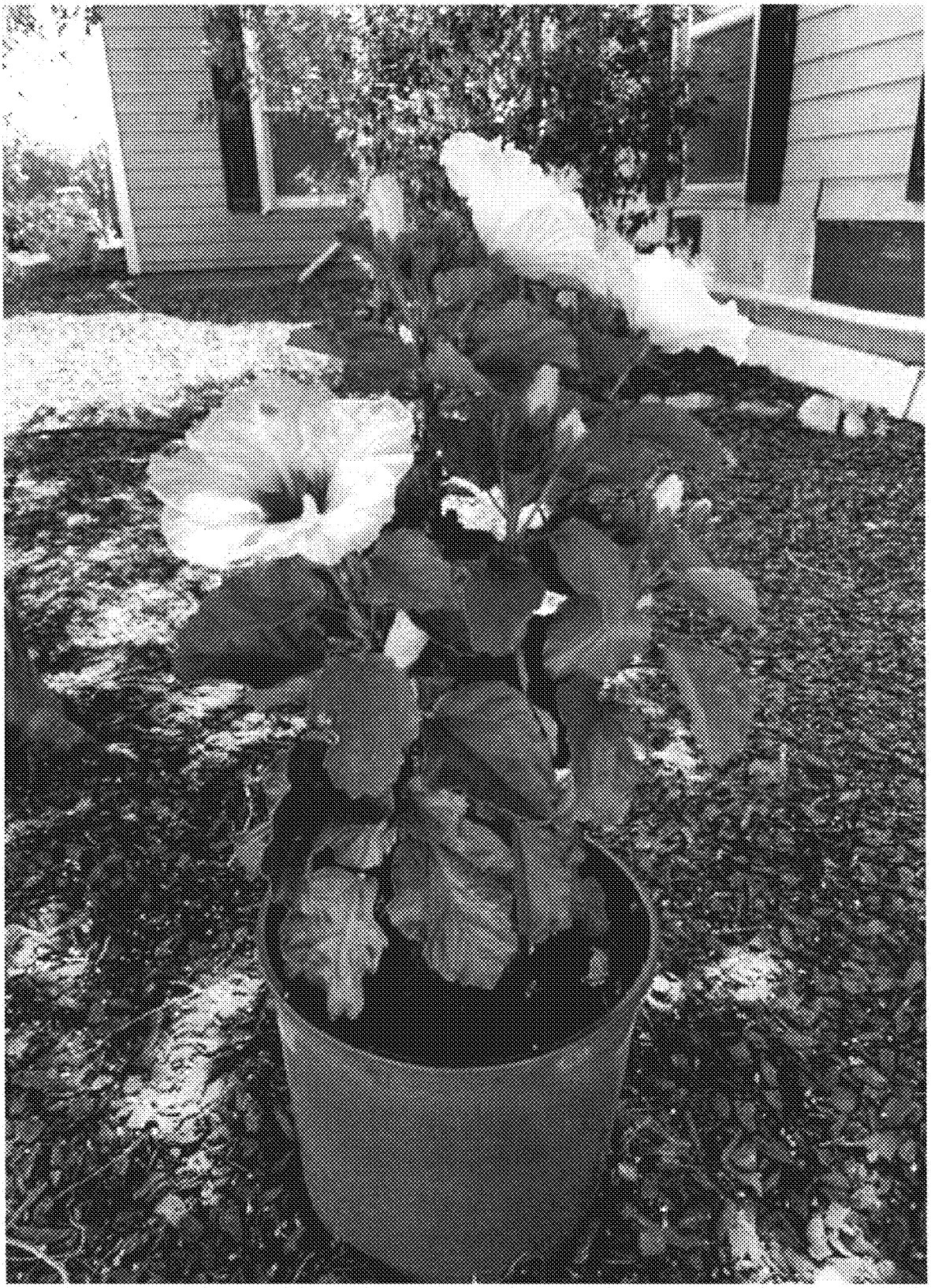
FIG. 2 illustrates a close-up view of an entire plant of the new variety.

The following detailed description sets forth the characteristics of the new variety. The plants were grown in a greenhouse with bottom heat in boxed, 1 yard soil containers. The color readings and measurements were taken indoors under natural light in a greenhouse on approximately three year old plants. Color references are primarily to the Munsell Color Chart (accessed online in 2022) and The 1995 R.H.S. Colour Chart, 3rd Edition, except where general color terms are used.

PLANT

Time to initiate roots: About 12 days at an average of 24° C.
Time to develop roots: About 50 days at an average of 21-24° C.
Time to produce a finished flowering plant from a rooted cutting: About 12-16 weeks in a 1 gallon/20.0 cm diameter container.
Specific disease/pest resistance: Resistance to whitefly (*Trialeurodes vaporariorum*) and bacterial leaf spot (*Pseudomonas* spp.).
Heat/cold tolerance: Thrives above 13° C., but expires at temperatures of 0° C. and below.
Drought tolerance: Moderate to none.
Plant:
- *Type*.—Tropical, ornamental shrub.
- *Habit*.—Upright; bush-like.
- *Height*.—1.5 m.
- *Spread*.—1.5 m.
- *Vigor*.—Moderate.
- *Rooting*.—Coarse and well-branched.

Stem:
- *Number per plant*.—15.
- *Length*.—61.0 cm.
- *Width*.—1.3 cm.
- *Texture*.—Immature: Smooth, green, semi-hard wood. Mature: Medium-textured, brown, hard wood.
- *Strength*.—Moderate and flexible.
- *Branch arrangement*.—Alternate.
- *Internode length*.—3.8-5.1 cm.
- *Color*.—Immature: 10GY 5/8. Mature: 10YR 2/6.
- *Stipules*.—Number per node: 2. Shape: Pointed. Length: 0.6 cm. Width: 1.6 mm. Surface texture: Smooth. Apex: Acute. Base: Attached. Margin: Entire. Color: 10GY 5/8.

Foliage:
- *Arrangement*.—Alternate.
- *Size of leaf*.—Length: 15.2 cm. Width: 14.0 cm.
- *Shape of leaf* (*generally*).—Cordate/oval.
- *Shape of apex*.—Mucronate/cuspidate.
- *Shape of base*.—Rounded/cordate.
- *Texture*.—Upper surface: Semi-abrasive and shiny. Lower surface: Semi-abrasive.
- *Margin type*.—Moderately serrate.
- *Color*.—Young leaves: Upper surface: 10GY 4/10. Lower surface: 10GY 6/10. Mature leaves: Upper surface: 10GY 4/10. Lower surface: 10GY 6/10.
- *Veins*.—Venation type: Netted. Color: Upper surface: 5GY 7/8. Lower surface: 5GY 7/8.
- *Petiole*.—Length: 5.1 cm. Diameter: 3.2 mm. Texture: Smooth. Color: 10GY 5/8.

FLOWERS

Buds (described in a tight/not swollen/not opened state):
- *Shape*.—Urn.
- *Diameter*.—1.3 cm.
- *Length*.—3.2 cm.
- *Color*.—10GY 6/10, but 2.5Y 9/12 when pushing color/swollen/not yet opened.

Natural flowering season: May to October in Azusa, Calif.
Flower type and habit: Complete and single.
Fragrance: Mild floral.
Flowers:
- *Number per stem*.—1-7.
- *Overall depth*.—12.7 cm.
- *Overall diameter*.—20.3 cm.
- *Shape*.—Stellate.
- *Lastingness*.—1-3 days on the plant.
- *Petals*.—Number: 5. Arrangement: Open. Length: 10.2 cm. Width: 7.6 cm. Shape: Oblanceolate. Apex: Round, with incisions absent. Base: Acute. Margin: Entire, with weak undulation intensity. Texture/appearance: Upper surface: Soft and smooth. Lower surface: Semi-abrasive. Color: When opening: Upper surface: 7.5Y 10/2. Lower surface: 5Y 9/10 that transitions to 7.5Y 10/2 at the center. Fully opened: Upper surface: 7.5Y 10/2 and a 2.5R 2/10 throat. Lower surface: 7.5Y 10/2. Eye zone: Size: Small. Extension length: Short. Color: 2.5R 2/10.
- *Calyx*.—Form: Free. Overall length: 2.5 cm. Overall diameter: 2.5 cm. Sepals/calyx lobes: Number: 7. Shape: Pointed. Apex: Pointed. Margin: Entire. Texture: Semi-abrasive. Color: Outer surface: 10GY 5/8. Inner surface: 10GY 6/10.
- *Epicalyx*.—Average number: 7 per flower. Length: Fused at base — 2.5 cm. Width: 2.5 cm. Texture: Semi-abrasive. Color: 2.5GY 6/14.
- *Bracts*.—Location: Part of the epicalyx — encircling the true calyx at the base of the sepals. Number: 2. Position: Opposite. Length: 0.6 cm. Width: 1.6 mm. Shape: Pointed. Apex: Pointed. Base: Attached. Margin: Entire. Texture/appearance: Upper surface: Semi-abrasive. Lower surface: Semi-abrasive. Color: Outer surface: 10GY 6/10. Inner surface: 10GY 6/10.
- *Peduncle*.—Length: 8.9 cm. Diameter: 3.2 mm. Strength: Strong. Angle: 45°. Texture: Smooth. Color: 10GY 6/10.

Reproductive organs:
- *Gynoecium*.—Pistils: Number: 1. Length: 8.9 cm. Stigma: Number: 5. Shape: Round. Length: 3.2 mm. Diameter: 3.2 mm. Color: 2.5YR 8/14. Style: Length: 0.6 cm. Width: 3.2 mm. Color: White with a pale hue of 7.5Y 10/2 and a 2.5R 2/10 base. Ovary: Shape: Urn. Length: 0.6 cm. Width: 0.6 cm. Color: 2.5R 2/10.
- *Androecium*.—Stamens: Number: Approximately 50. Position: Below the stigma on the style. Anther: Shape: Round. Diameter: 1.6 mm. Color: 7.5Y 9/12. Filament: Length: 3.2 mm. Width: 1.6 mm. Color: White with a pale hue of 7.5Y 10/2. Pollen: Color: 7.5Y 9/12. Amount (generally): Abundant.

SEEDS

Seeds:
- *Number*.—15.
- *Color*.—200A.
- *Length*.—5.0 mm.
- *Width*.—4.0 mm.

I claim:

1. A new and distinct variety of *Hibiscus* plant named 'JBG AH-51', substantially as illustrated and described herein.

* * * * *